(12) United States Patent
Quintero

(10) Patent No.: US 11,191,531 B1
(45) Date of Patent: Dec. 7, 2021

(54) AMNIO OPENING OCCLUSION DEVICE WITH REMOVAL ELEMENT

(71) Applicant: Ruben Quintero, Miami, FL (US)

(72) Inventor: Ruben Quintero, Miami, FL (US)

( * ) Notice: Subject to any disclaimer, the term of this patent is extended or adjusted under 35 U.S.C. 154(b) by 0 days.

(21) Appl. No.: 17/062,104

(22) Filed: Oct. 2, 2020

(51) Int. Cl.
*A61B 17/00* (2006.01)
*A61B 17/42* (2006.01)

(52) U.S. Cl.
CPC .............. *A61B 17/0057* (2013.01); *A61B 2017/00606* (2013.01); *A61B 2017/00867* (2013.01); *A61B 2017/4216* (2013.01)

(58) Field of Classification Search
CPC ...... A61B 17/0057; A61B 2017/00606; A61B 2017/00592; A61B 2017/00575
See application file for complete search history.

(56) References Cited

U.S. PATENT DOCUMENTS

| | | | | |
|---|---|---|---|---|
| 5,846,261 | A * | 12/1998 | Kotula | A61F 2/01 606/213 |
| 8,715,314 | B1 * | 5/2014 | Janardhan | A61B 17/22031 606/200 |
| 2005/0228434 | A1 * | 10/2005 | Amplatz | A61B 17/12109 606/200 |
| 2006/0224183 | A1 * | 10/2006 | Freudenthal | A61B 17/12027 606/213 |
| 2006/0247680 | A1 * | 11/2006 | Amplatz | A61B 17/12022 606/213 |
| 2008/0262518 | A1 * | 10/2008 | Freudenthal | A61B 17/12122 606/151 |
| 2012/0065667 | A1 * | 3/2012 | Javois | A61B 17/12122 606/213 |
| 2012/0271337 | A1 * | 10/2012 | Figulla | A61B 17/12022 606/191 |
| 2013/0131717 | A1 * | 5/2013 | Glimsdale | A61B 17/0057 606/213 |
| 2015/0133989 | A1 * | 5/2015 | Lubock | A61B 17/0057 606/200 |
| 2016/0287228 | A1 * | 10/2016 | Quintero | A61B 17/0057 |
| 2017/0014113 | A1 * | 1/2017 | Ma | A61B 17/12122 |
| 2017/0014114 | A1 * | 1/2017 | Rafiee | A61B 17/12031 |

* cited by examiner

*Primary Examiner* — Alexander J Orkin
(74) *Attorney, Agent, or Firm* — Mark Terry

(57) ABSTRACT

A collapsible medical device is used for occluding an opening used for fetoscopic surgery. The device includes tubular woven metal fabric composed of braided metal strands, said woven metal fabric having an expanded preset configuration comprising an hourglass-shaped element and a waist element at a midpoint, wherein each end of the hourglass-shaped element has a diameter of about 5 mm, wherein the waist element has a diameter that is less than a diameter of each end of the hourglass-shaped element, said woven metal fabric further includes a bulbous element coupled to one end of the hourglass-shaped element via a shaft, wherein the woven metal fabric is deformable to a lesser cross-sectional dimension for delivery through a channel in a patient's body to said opening, and the woven metal fabric having a memory property whereby the medical device tends to return to said expanded preset configuration when unconstrained.

18 Claims, 9 Drawing Sheets

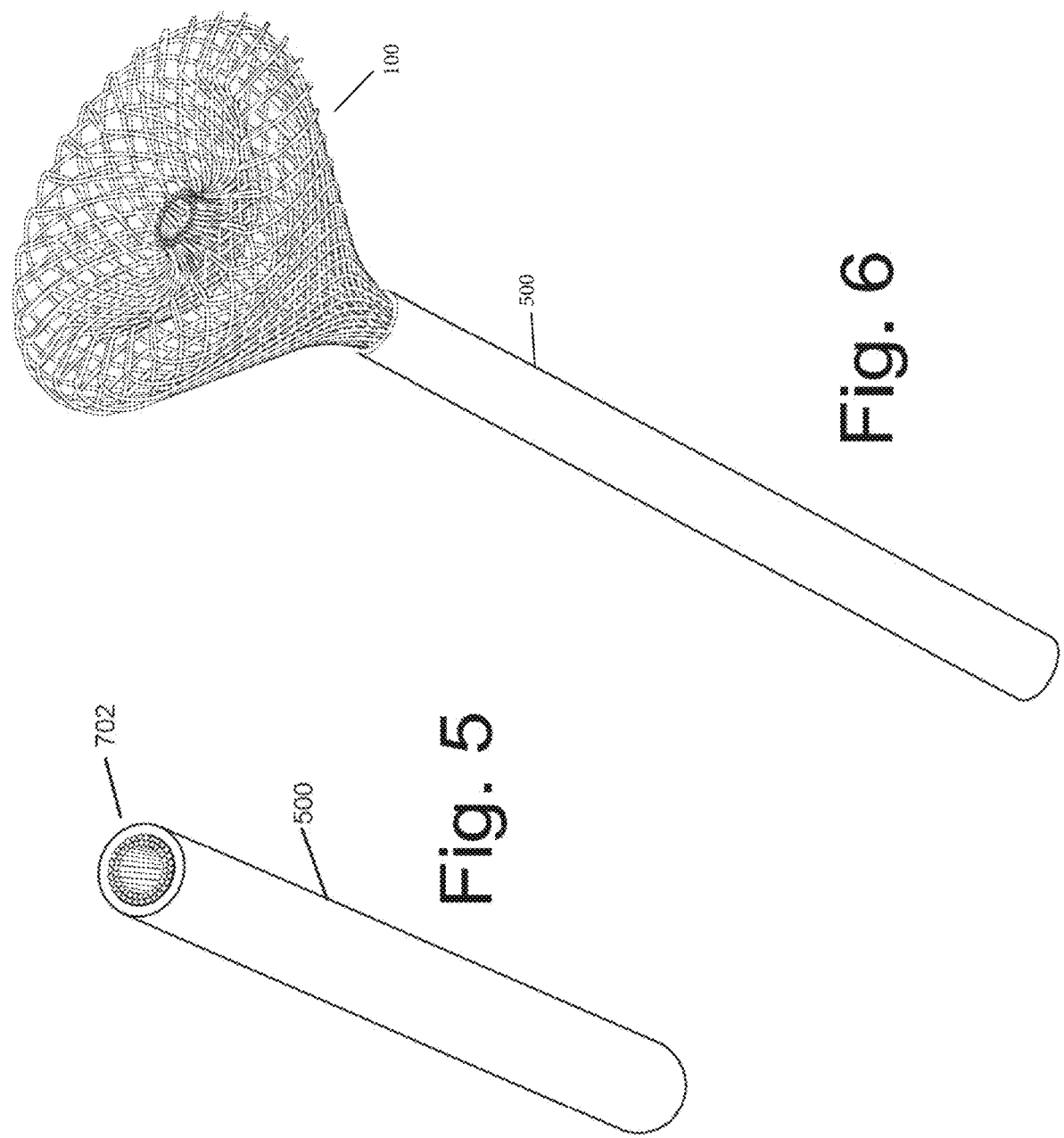

AMNIO OPENING OCCLUSION DEVICE WITH REMOVAL ELEMENT

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The disclosed embodiments relate to the field of medical devices and more specifically to medical devices used to close or occlude an opening in a patient.

BACKGROUND

Fetal surgery is any of a broad range of surgical techniques and processes that are used to treat birth defects or other medical problems in fetuses who are still in the pregnant uterus. Open fetal surgery involves completely opening the uterus to operate on the fetus. Minimally invasive endoscopic fetal surgery (operative fetoscopy) uses small skin incisions and is performed using endoscopy and sonography. Minimally-invasive fetoscopic surgery uses real-time video imagery from fetoscopy and ultrasonography to guide very small surgical instruments into the uterus in order to perform the surgical tasks. Less invasive than open fetal surgery, some fetal surgeries can be achieved with just a small incision on the skin of the mother (percutaneous), though in some cases it may require that a small opening be made in the mother's abdomen. The fact that it is less invasive reduces the mother's postoperative recovery and lessens the troubles with preterm labor. Minimally invasive fetoscopic surgery has proven to be very useful for most, but not all, fetal or placental conditions One of the problems associated with even minimally invasive fetoscopic surgery is the opening that is made in the pregnant patient's uterus in order to operate on the fetus or the placenta. This opening, which results from the insertion of the trocar or other medical instruments, can be the cause of later problems in the patient. Said opening can cause the fetal membrane to separate from the uterine wall, otherwise known as chorioamniotic separation or membrane detachment, which can lead to complications. Chorioamniotic separation may result either in extravasation of the amniotic fluid between the amnion and the chorion, which may hinder further access to the amniotic cavity, or in gross leakage of fluid via the patient's vagina. In the latter case, the pregnancy is at risk for being lost due to premature rupture of said membranes. Said leakage through the opening and out of the vagina can further result in infection or other difficulties.

Therefore, there exists a need for improvements over the prior art, and more particularly for a more efficient way of treating the opening that is made in the pregnant patient's body during fetoscopic surgery.

SUMMARY

In one embodiment, a medical device is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The disclosed collapsible medical device is used for occluding an opening used for fetoscopic surgery. The device comprises tubular woven metal fabric comprised of a plurality of braided metal strands, said woven metal fabric having an expanded preset configuration comprising an hourglass-shaped element and a waist element at a midpoint of the hourglass-shaped element; wherein each end of the hourglass-shaped element has a diameter of about 5 mm; wherein the waist element has a diameter that is less than a diameter of each end of the hourglass-shaped element; said expanded preset configuration of said woven metal fabric further comprising a bulbous element coupled to one end of the hourglass-shaped element via a shaft; wherein the woven metal fabric is deformable to a lesser cross-sectional dimension for delivery through a channel in a patient's body to said opening used for fetoscopic surgery; and the woven metal fabric having a memory property whereby the medical device tends to return to said expanded preset configuration when unconstrained.

BRIEF DESCRIPTION OF THE DRAWINGS

The accompanying drawings, which are incorporated in and constitute part of this specification, illustrate embodiments of the claimed subject matter and together with the description, serve to explain the principles of the claimed embodiments. The embodiments illustrated herein are presently preferred, it being understood, however, that the claimed embodiments are not limited to the precise arrangements and instrumentalities shown, wherein:

FIG. 5 is a top perspective view of a delivery tube including the collapsible medical device in a fully retracted mode, according to one embodiment.

FIG. 6 is a top perspective view of the delivery tube including the collapsible medical device in a semi-deployed mode, according to one embodiment.

DETAILED DESCRIPTION

Figure 1:
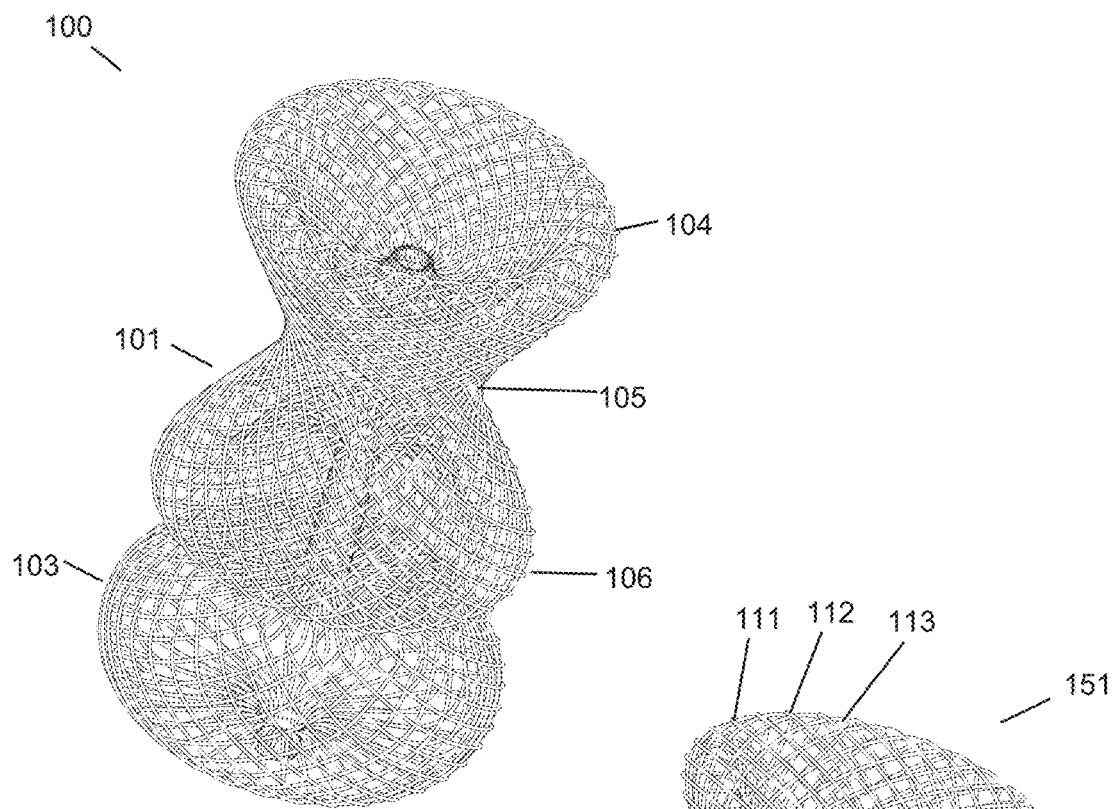
FIG. 1 is a top perspective view of the collapsible medical device in a fully deployed mode, according to one embodiment.
Figure 2:
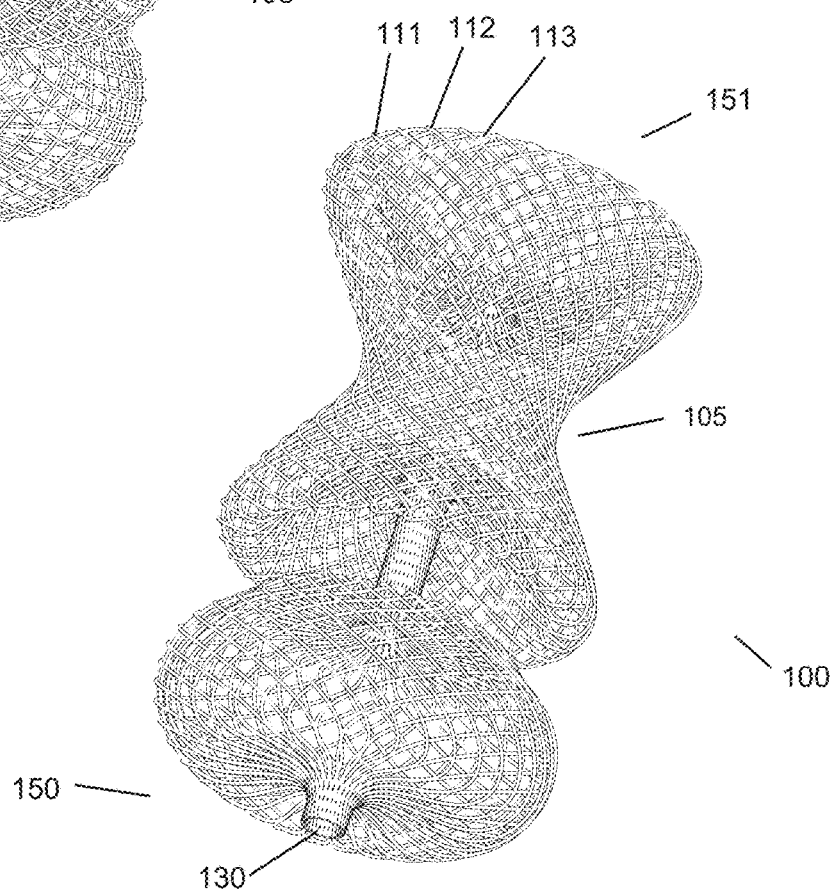
FIG. 2 is a bottom perspective view of the collapsible medical device in a fully deployed mode, according to one embodiment.
Figure 3:
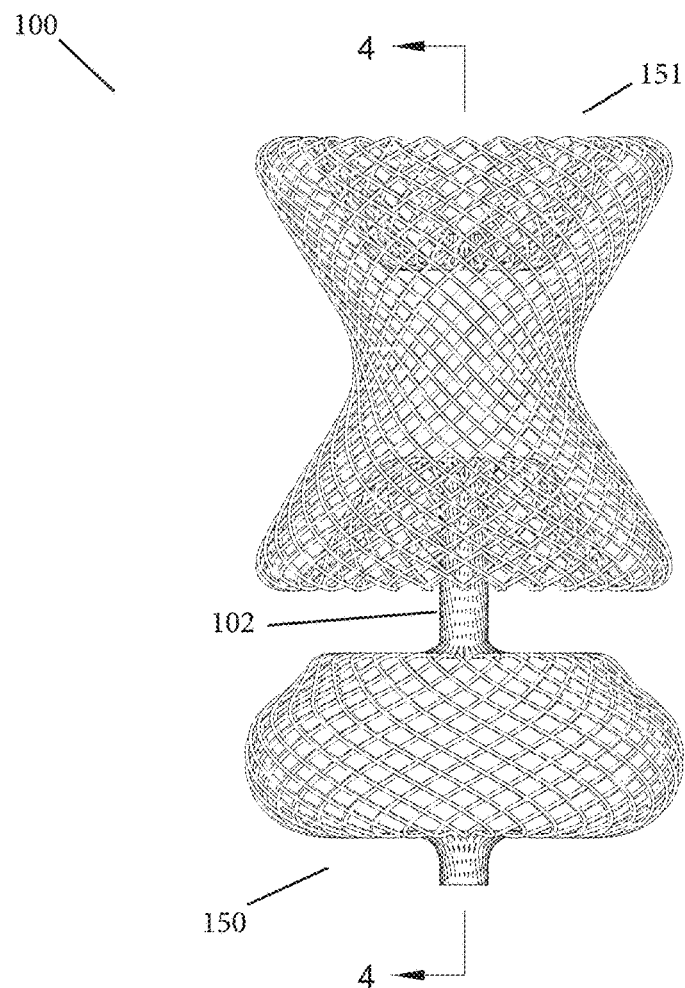
FIG. 3 is a side view of the collapsible medical device in a fully deployed mode, according to one embodiment.
Figure 4:
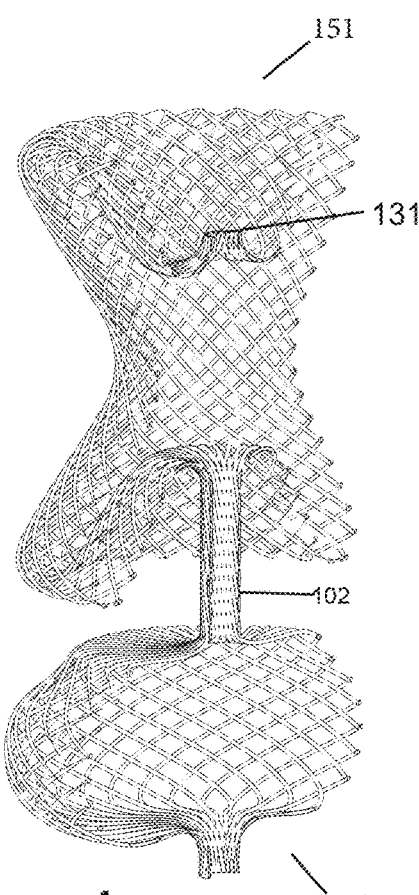
FIG. 4 is a side cross-sectional view of the collapsible medical device in a fully deployed mode, according to one embodiment.

The disclosed embodiments improve upon the problems with the prior art by providing a collapsible medical device that is easily deployed for use in occluding an opening used for fetoscopic surgery. The disclosed embodiments improve over the prior art by providing a safe, inexpensive and user-friendly method for occluding an opening used for fetoscopic surgery. Additionally, the disclosed embodiments improve over the prior art by providing a medical device that prevents or reduces the incidence of chorioamniotic separation or membrane detachment, which can otherwise lead to complications. Further, the disclosed embodiments reduce the likelihood of losing a pregnancy due to premature rupture of said membranes, as well as the likelihood of infection and other maternal and fetal difficulties. Also, the disclosed embodiments improve over the prior art by providing a medical device that is easily deployable via a catheter or trocar, thereby reducing the number or size of incisions that must be made in a patient's body. Additionally, the disclosed embodiments allow for the easy removal of the device from the patient, via a structural removal element, at a later time, such as after the patient gives birth.

The claimed embodiments shall now be described with reference to FIGS. 1-9 where there is shown generally the device 100 suitable for occluding an opening in a patient's body, such as an opening in a uterus made during fetoscopic surgery. In its relaxed, unstretched state (see FIGS. 1-4), the device generally includes a tubular woven metal fabric comprised of a plurality of braided metal strands (111, 112, 113), said woven metal fabric having an expanded preset configuration comprising an hourglass-shaped element 101 having a waist element 105 at a midpoint of the hourglass-shaped element, and a bulbous element 103 coupled to the hourglass-shaped element 101 via a shaft 102. In one embedment, each end of the hourglass-shaped element (i.e., the thicker portions of the hourglass element at each end) has a diameter of about 8-10 mm. The waist element may have a diameter that is less than a diameter of each end of the hourglass-shaped element. The expanded preset configuration of said woven metal fabric may further comprise a bulbous element 103 coupled to one end of the hourglass-shaped element via a woven shaft 102. The woven metal fabric is deformable to a lesser cross-sectional dimension for delivery through a channel in a patient's body to said opening used for fetoscopic surgery. The woven metal fabric may have a memory property whereby the medical device 100 tends to return to said expanded preset configuration when unconstrained.

Figure 8:
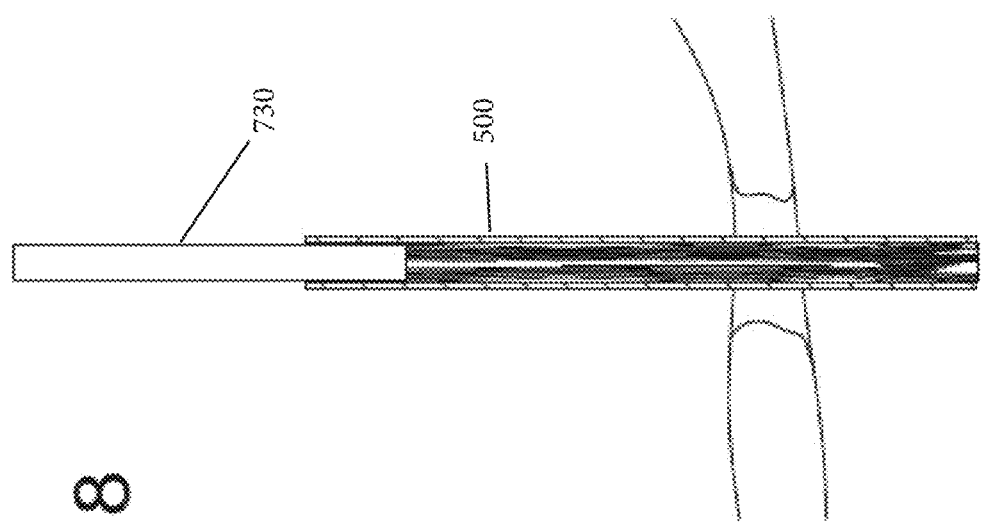
FIG. 8 is a side cross-sectional view of the delivery tube being inserted into a patient's opening, according to one embodiment.

It should be noted that the bulbous element 103 is configured for removal of the device 100 at a time later that its deployment, such as after the patient has given birth. For this reason, the bulbous element 103 may be referred to as a removal element, which refers to the ability to remove the device 100 from the patient by providing an element (103) that is easily grabbed and may be pulled with enough force to remove device 100 from the patient without causing unnecessary tissue damage to the patient. The shape of bulbous element 103 is configured to allow a surgeon to easily grab the element 103 using a medical instrument, such as obstetrical forceps. The construction of bulbous element 103 is configured to allow the surgeon to pull the element 103 while maintaining the structural integrity of the device 100, for the purpose of removal of the entire device 100, all in one piece, from the patient. In one embodiment, when the bulbous element 103 is pulled, the device 100 collapses, as shown in FIGS. 5 and 8, for easier and quicker removal from the patient.

FIGS. 1-4 shows that the device 100 includes two spaced apart occluding members 104, 106 (shaped like truncated cones, for example) interconnected by a flexible, resilient center portion 105 (called a waist). The first cone shaped element 104 (truncated cone) is coupled to the second cone shaped element 106 (also a truncated cone) at the waist 105. Note that the first cone shaped element 104 is oriented in an inverted manner with respect to the second cone shaped element such that the truncated tip of the first cone shaped element 104 is coupled to the truncated tip of second cone shaped element 106. Note also that the first cone shaped element 104 and the second cone shaped element 106 are arranged such that the their longitudinal axes are aligned and colinear, wherein the longitudinal axis of a truncated cone is defined as a line that extends from a midpoint of the circular base of the cone to the center of the truncated tip of the cone.

The members 104, 106 and the waist 105 comprise the hourglass-shaped element 101. The plurality of braided wires (111, 112, 113) form an outer and inner surface of each member 104, 106, the waist 105, bulbous element 103 and the shaft 102. The shape of the hourglass-shaped element 101 ensures that the members 104, 106 and the waist 105 contact the wall of the opening being occluded. In the preferred embodiment, the occluding device is formed from a single continuous tubular metal fabric. The tubular fabric is formed from a plurality of wire strands having a predetermined relative orientation between the strands. This tubular fabric is known in the fabric industry as a tubular braid.

Note that the elements of the device 100, including the hourglass-shaped element 101, the bulbous element 103 and the shaft 102, are all composed of the tubular woven metal fabric comprised of a plurality of braided metal strands (111, 112, 113), wherein said woven metal fabric has an expanded preset configuration that includes an inner surface and an outer surface of the device 100. That is, in the expanded preset configuration, the device 100 comprises a three-dimensional shape with an interior volume that is hollow and a surface that is comprised of the tubular woven metal fabric.

The device 100 of the claimed embodiments has a specific shape which is particularly well suited for occluding an opening made in a uterus during fetoscopic surgery. Fetoscopic surgery is a form of fetal intervention in the treatment of birth defects and other fetal problems. The device has a relaxed low-profile configuration and may include one or more clamps (at 130, 131, for example) that allow attachment of the device to an end of a guidewire 730. The first clamp 130 may be located at a proximal end 150 of the device 100 and the second clamp 131 may be located at a distal end 151 of the device 100. When the device 100 is in a relaxed state, the occluding members 104, 106 expand outwards or perpendicular to the longitudinal axis of the device. In this manner, when the occluding members are pulled apart, the spring-like action of the device will cause the exterior surface of the hourglass-shaped element 101 to fully engage the sidewall of the opening. FIGS. 8-11 illustrate sequentially the stretching, spring-like action of the device.

The disclosed embodiments are formed from a resilient metal fabric a plurality of resilient strands or wires (111, 112, 113), with the metal fabric being formed by braiding the resilient strands to create a resilient material. This braided fabric is then deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric so treated defines a relaxed state of the medical device 100 which can be stretched or expanded and deployed through a catheter into a channel in the patient's body.

Figure 7:
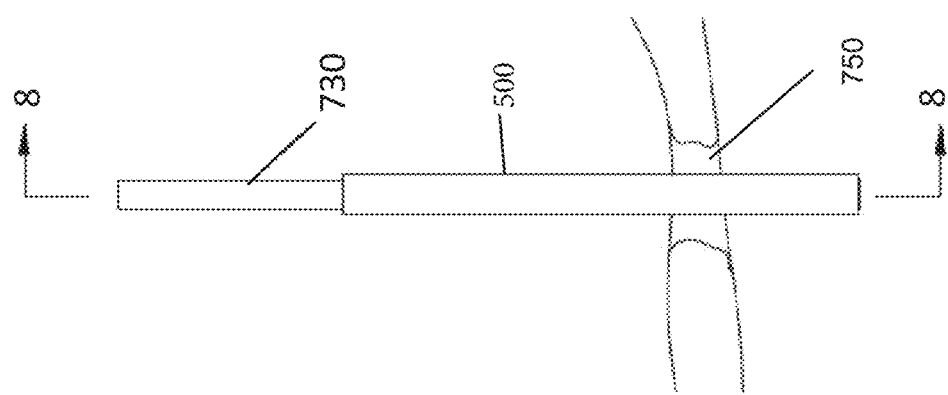
FIG. 7 is a side view of the delivery tube being inserted into a patient's opening, according to one embodiment.
Figure 9:
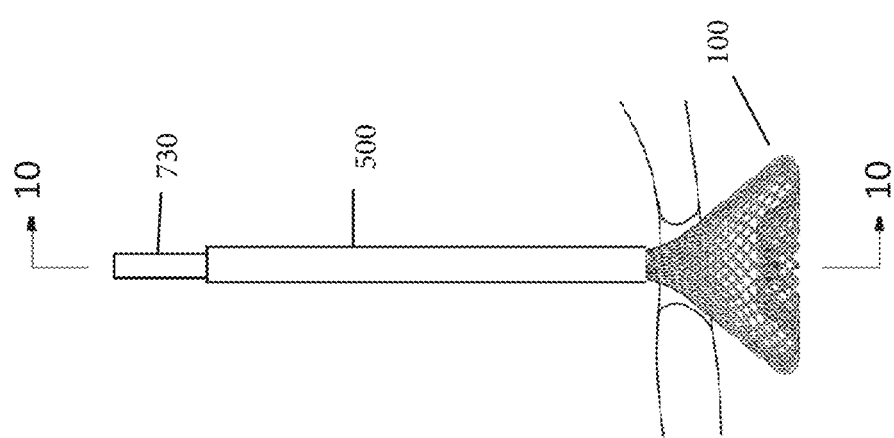
FIG. 9 is a side view of the delivery tube having been inserted into the patient's opening, wherein the collapsible medical device is in a semi-deployed mode, according to one embodiment.
Figure 10:
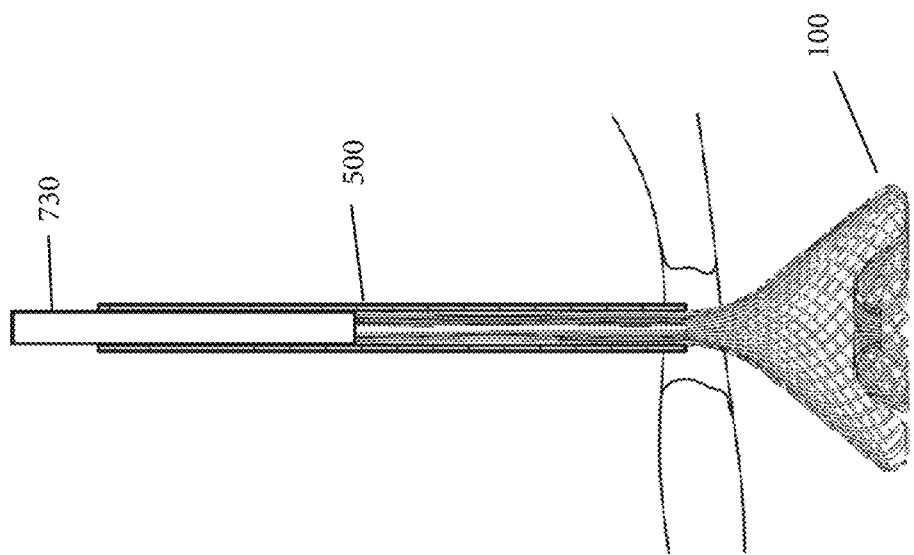
FIG. 10 is a side cross-sectional view of the delivery tube having been inserted into the patient's opening, wherein the collapsible medical device is in a semi-deployed mode, according to one embodiment.
Figure 11:
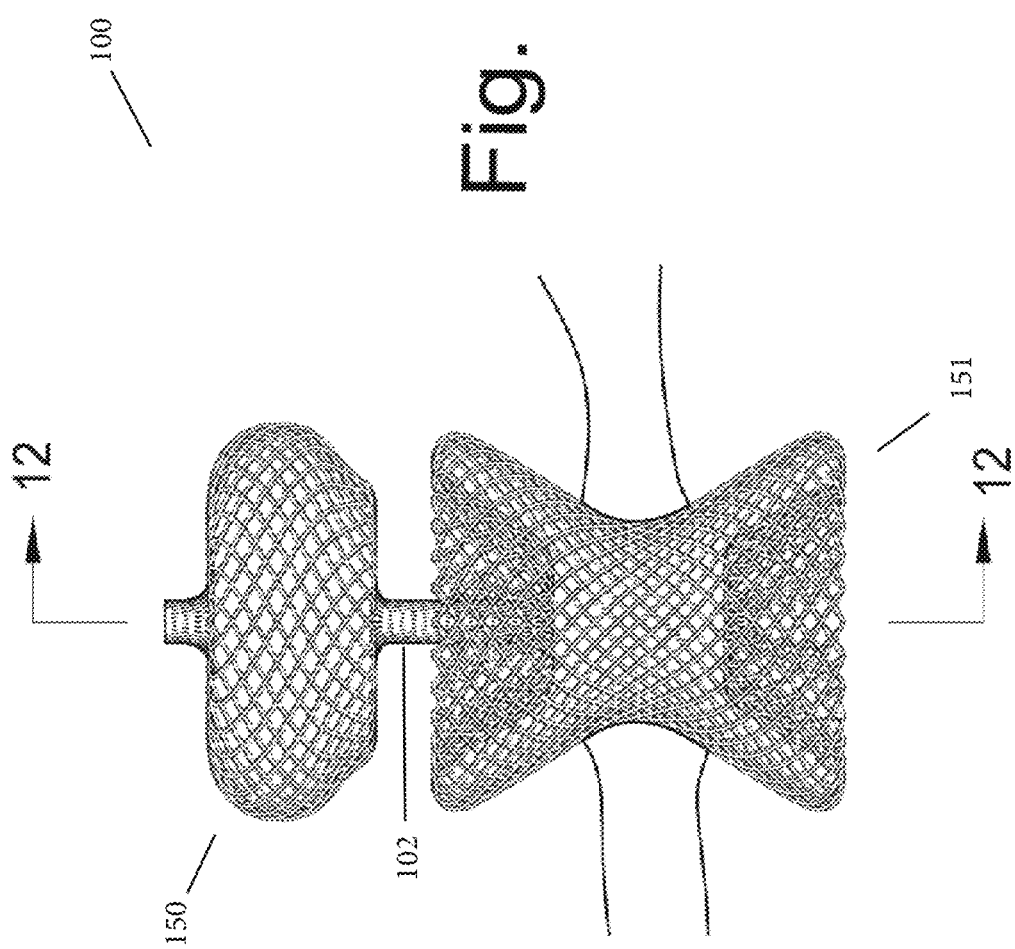
FIG. 11 is a side view of the collapsible medical device in a fully-deployed mode in the patient's opening, according to one embodiment.
Figure 12:
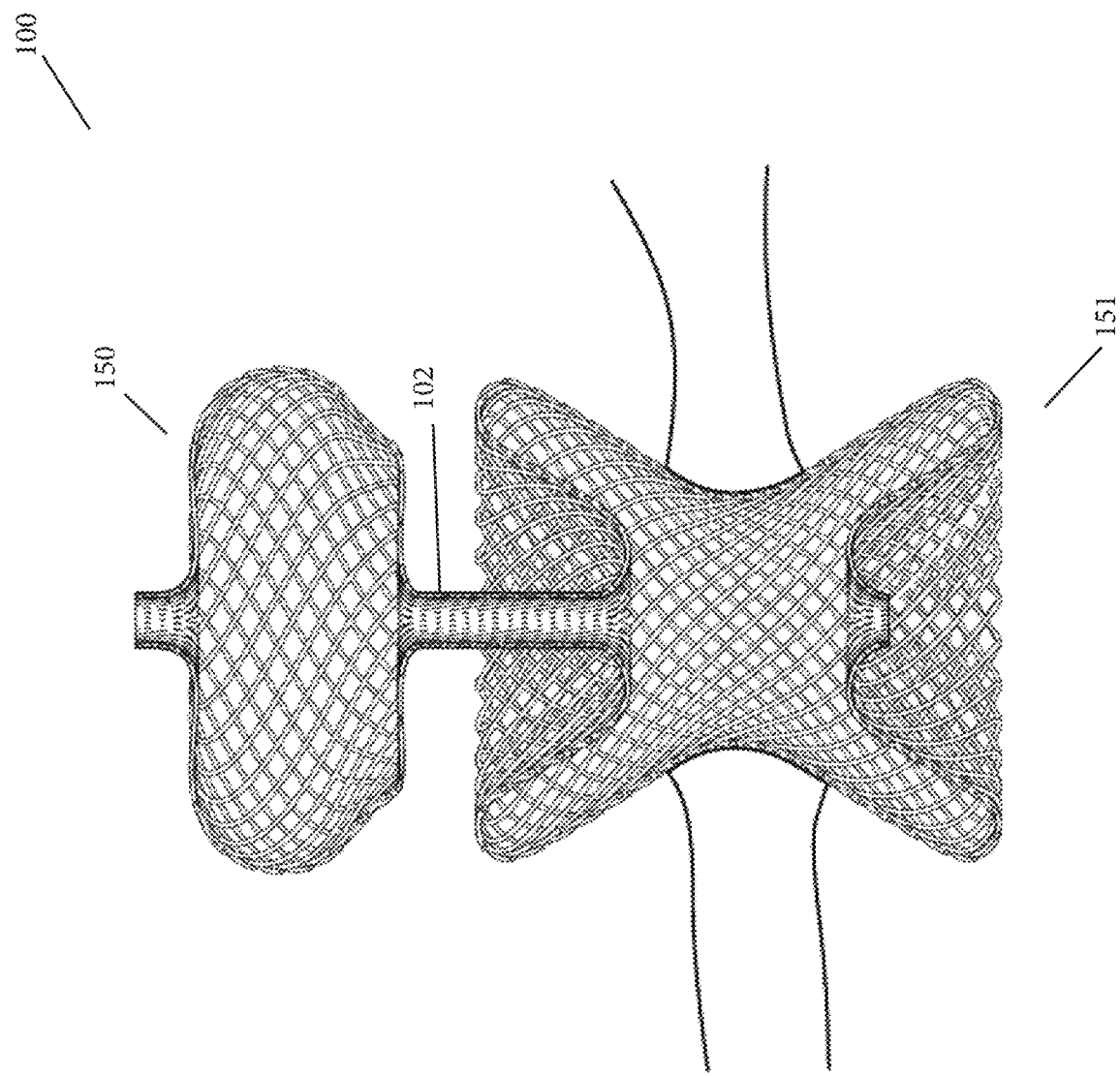
FIG. 12 is a side cross-sectional view of the collapsible medical device in a fully-deployed mode in the patient's opening, according to one embodiment.

The claimed embodiments shall now be described with reference to FIGS. 5-12 where the device 100 is shown in the process of a surgery for occluding an opening in a patient's body, such as an opening in a uterus made during fetoscopic surgery. In use, a catheter 500 is positioned and advanced in a patient's body such that the distal end 702 of the catheter is adjacent a desired treatment site for occluding an opening or treating a physiological condition, as shown in FIG. 7. The medical device 100 is then stretched and inserted into the lumen of the catheter, as shown in FIGS. 5 and 8. FIGS. 5, 7 and 8 show views of the device 100 in fully retracted mode within the catheter, which is already located at the treatment site. The device 100 is then urged through the catheter by the guidewire 730 and out the distal end, as shown in FIGS. 6, 9 and 10, which show the device 100 in a semi-deployed mode exiting the catheter at the treatment site. Subsequently, the device 100 is pushed completely out of the catheter, and, due to its shape memory property, it will tend to substantially return to its relaxed state adjacent the treatment site, as shown in FIGS. 11 and 12, which shows the device 100 in a fully deployed state at the treatment site. The guidewire is then released from the clamp(s) and removed.

A catheter 500 or other suitable delivery device may be positioned within a channel in a patient's body to place the distal end 702 of the delivery device adjacent the desired treatment cite, such as immediately adjacent (or even within) the opening 750 in the patient, such as in an organ, as shown in FIGS. 7-8. The guide wire 730 can take any suitable shape, but desirably comprises an elongate flexible metal shaft having a threaded distal end. The guide wire can be used to urge the medical device 100 through the lumen of the catheter 500 for deployment in an opening of a patient's body, as shown in FIGS. 9 and 10. When the device is fully deployed out the distal end of the catheter (as shown in FIGS. 11-12), the device will still be retained by the guide wire. Once the medical device is properly positioned within the opening (as shown in FIGS. 11-12), the distal end of the catheter may be pressed against the medical device and the guidewire can be rotated about its axis to unscrew the medical device from the threaded distal end of the guidewire. The catheter and guidewire are then withdrawn.

By keeping the medical device 100 attached to the guide wire, the operator can retract the device for repositioning relative to the opening 750, if it is determined that the device is not properly positioned within the opening. A threaded clamp at 130 attached to the medical device allows the operator to control the manner in which the medical device is deployed out the distal end of the catheter. When the device exits the catheter, it will tend to resiliently return to a preferred relaxed shape, as shown in FIGS. 11 and 12. When the device springs back into this shape, it may tend to act against the distal end of the catheter effectively urging itself forward beyond the end of the catheter. This spring action could conceivably result in improper positioning of the device if the location of the device is critical, such as where it is being positioned in an opening. Since the threaded clamp can enable the operator to maintain a hold on the device during deployment, the spring action of the device can be controlled by the operator to ensure proper positioning during deployment.

During the initial deployment, the medical device 100 can be collapsed into its collapsed configuration and inserted into the lumen of the catheter 500, as shown in FIGS. 5 and 8. The collapsed configuration of the device may be of any shape suitable for easy passage through the lumen of the catheter and proper deployment out the distal end of the catheter. For example, the device may have a relatively elongated collapsed configuration wherein the device is stretched along its longitudinal axis, which extends through a midline axis of the hourglass shaped element 101, the shaft 102 and the bulbous element 103. This collapsed configuration can be achieved simply by stretching the device generally along its longitudinal axis, e.g. by manually grasping the clamps 130, 131 and pulling them apart, which will tend to collapse the relaxed diameter portions of the device inwardly toward the device's longitudinal axis. Loading the device into the catheter may be done at the time of implantation.

Upon full deployment, the device 100 is used to occlude an opening in the patient's body, and once this is accomplished (as shown in FIGS. 11-12), the catheter is removed from the patient's body. This leaves the medical device deployed in the patient's opening 750 so that it may occlude the opening in the patient's body. Before removing the catheter, it may be necessary to detach the medical device from the guidewire before removing the catheter and the guidewire. In one embodiment, the opening 750 may comprise an opening, hole or orifice made during fetoscopic surgery, or the opening may comprise an abnormal opening, hole or orifice that arose out of a medical condition.

Those skilled in the art will appreciate that the device is sized in proportion to the opening to be occluded. The diameter of each occluding members 104, 106 and waist 105 may be varied as desired for differently sized openings in the uterus. If the size of the opening is 3.8 mm, then the size of the occluding members is 5 mm; if the size of the opening is 5 mm, then the size of the occluding members is 7 mm; if the size of the opening is 7 mm, then the size of the occluding members is 9-10 mm Both occluding members may be the same size. Further, the thickness of the waist may be varied depending upon the thickness of the uterine wall and the fetal membrane, and may range between 0.5 to 1 cm.

In one embodiment, the claimed device 100 includes a bulbous element 103, which is coupled to the hourglass shaped element 101 via a shaft 102. The purpose of the bulbous element is to provide a structural element, also referred to as a removal element, that can be grabbed and pulled at the time of removal of the device 100 from the patient's body. In certain fetal surgeries, the device 100 is only meant to reside within the patient for a limited amount of time. For example, in one embodiment, the device 100 is only meant to reside within the patient during pregnancy, after which the device is to be removed. After the device 100 has resided within the patient's body for a certain period of time, however, the device can become lodged within the patient's body due to tissue growth, debris or growth due to pregnancy. In this case, the bulbous element 103 provides a structural element, integrated into the tubular woven metal fabric that comprises the hourglass-shaped element 101, such that the bulbous element can be grabbed and pulled at time of removal of the device 100 from the patient's body, such that the device 100 may be removed all at once and intact. When placed in the uterus, the device 100 does not promote cell ingrowth and is configured to be removed at the time of delivery of the baby.

In one embodiment, the women metal fabric of the claimed device 100 may comprise a shape-memory alloy that can be deformed when cold but returns to its pre-deformed ("remembered") shape when heated. Said shape-memory alloy may also be called memory metal, memory alloy, smart metal, smart alloy, or muscle wire. In another embodiment, the women metal fabric of the claimed device 100 may comprise a shape-memory polymer, which is a polymeric smart material with the ability to return from a deformed state (temporary shape) to its original (permanent) shape induced by an external stimulus (trigger), such as a temperature change.

Although specific embodiments have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the invention.

We claim:

1. A collapsible medical device for occluding an opening used for fetoscopic surgery in a patient, comprising:
    a tubular woven metal fabric comprised of a plurality of braided metal strands, said woven metal fabric having an expanded preset configuration comprising an hourglass-shaped element having a first cone-shaped element coupled to a second cone-shaped element at a juncture that comprises a waist, and a preset collapsed configuration that deforms to a lesser cross-sectional dimension for delivery through a channel in the patient's body to said opening used for fetoscopic surgery, and wherein said woven metal fabric is configured to inhibit cell ingrowth when implanted in the patient;
    wherein the first and second cone-shaped elements each have a maximum diameter of about 5 mm;
    wherein the waist has a diameter between 0.5 to 1 cm;
    said expanded preset configuration of said woven metal fabric further comprising a shaft extending from a center of the first cone-shaped element and a bulbous element coupled to said shaft, wherein said bulbous element is configured for grabbing with forceps such that when the bulbous element is pulled for removing the collapsible medical device from the patient, said woven metal fabric collapses into the preset collapsed configuration while maintaining structural integrity of the woven metal fabric;
    the woven metal fabric having a memory property whereby the medical device returns to said expanded preset configuration when unconstrained.

2. The collapsible medical device of claim 1, wherein the first cone-shaped element coupled is the same size as the second cone-shaped element.

3. The collapsible medical device of claim 2, wherein the first cone-shaped element is oriented in an inverted matter with respect to the second cone-shaped element.

4. The collapsible medical device of claim 3, wherein the shaft is aligned with a longitudinal axis of the first and second cone shaped elements.

5. The collapsible medical device of claim 4, further comprising a clamp located at a distal end of the tubular woven metal fabric, the clamp configured for detachable coupling to a guidewire.

6. The collapsible medical device of claim 5, further comprising a second clamp located at a proximal end of the tubular woven metal fabric, the clamp configured for detachable coupling to a guidewire.

7. A collapsible medical device for occluding an opening used for fetoscopic surgery in a patient, comprising:
    a tubular woven metal fabric comprised of a single braided metal strand, said woven metal fabric having an expanded preset configuration comprising an hourglass-shaped element having a first cone-shaped element coupled to a second cone-shaped element at a juncture that comprises a waist, and a preset collapsed configuration that deforms to a lesser cross-sectional dimension for delivery through a channel in the patient's body to said opening used for fetoscopic surgery, and wherein said woven metal fabric is configured to inhibit cell ingrowth when implanted in the patient;
    wherein the first and second cone-shaped elements each have a maximum diameter of about 5 mm;
    wherein the waist has a diameter between 0.5 to 1 cm;
    said expanded preset configuration of said woven metal fabric further comprising a shaft extending from a center of the first cone-shaped element and a bulbous element coupled to said shaft, wherein said bulbous element is configured for grabbing with forceps such that when the bulbous element is pulled for removing the collapsible medical device from the patient, said woven metal fabric collapses into the preset collapsed configuration while maintaining structural integrity of the woven metal fabric;
    the woven metal fabric having a memory property whereby the medical device returns to said expanded preset configuration when unconstrained.

8. The collapsible medical device of claim 7, wherein the first cone-shaped element is the same size as the second cone-shaped element.

9. The collapsible medical device of claim 8, wherein the first cone-shaped element is oriented in an inverted matter with respect to the second cone-shaped element.

10. The collapsible medical device of claim 9, wherein the shaft is aligned with a longitudinal axis of the first and second cone shaped elements.

11. The collapsible medical device of claim 10, further comprising a clamp located at a distal end of the tubular woven metal fabric, the clamp configured for detachable coupling to a guidewire.

12. The collapsible medical device of claim 11, further comprising a second clamp located at a proximal end of the tubular woven metal fabric, the clamp configured for detachable coupling to a guidewire.

13. A collapsible medical device for occluding an opening used for fetoscopic surgery in a patient, comprising:
- a tubular woven polymer fabric comprised of a plurality of braided polymer strands, said woven polymer fabric having an expanded preset configuration comprising an hourglass-shaped element having a first cone-shaped element coupled to a second cone-shaped element at a juncture that comprises a waist, and a preset collapsed configuration that deforms to a lesser cross-sectional dimension for delivery through a channel in the patient's body to said opening used for fetoscopic surgery, and wherein said woven polymer fabric is configured to inhibit cell ingrowth when implanted in the patient;
- wherein the first and second cone-shaped elements each have a maximum diameter of about 5 mm;
- wherein the waist has a diameter between 0.5 to 1 cm;
- said expanded preset configuration of said woven polymer fabric further comprising a shaft extending from a center of the first cone-shaped element and a bulbous element coupled to said shaft, wherein said bulbous element is configured for grabbing with forceps such that when the bulbous element is pulled for removing the collapsible medical device from the patient, said woven polymer fabric collapses into the preset collapsed configuration while maintaining structural integrity of the woven polymer fabric;
- the woven polymer fabric having a memory property whereby the medical device returns to said expanded preset configuration when unconstrained.

14. The collapsible medical device of claim 13, wherein the first cone-shaped element coupled is the same size as the second cone-shaped element.

15. The collapsible medical device of claim 14, wherein the first cone-shaped element is oriented in an inverted matter with respect to the second cone-shaped element.

16. The collapsible medical device of claim 15, wherein the shaft is aligned with a longitudinal axis of the first and second cone shaped elements.

17. The collapsible medical device of claim 16, further comprising a clamp located at a distal end of the tubular woven polymer fabric, the clamp configured for detachable coupling to a guidewire.

18. The collapsible medical device of claim 17, further comprising a second clamp located at a proximal end of the tubular woven polymer fabric, the clamp configured for detachable coupling to a guidewire.

* * * * *